US009878906B2

(12) United States Patent
Schubert et al.

(10) Patent No.: US 9,878,906 B2
(45) Date of Patent: Jan. 30, 2018

(54) METHOD FOR PRODUCING ORGANOMETALLIC FRAMEWORK MATERIALS CONTAINING MAIN GROUP METAL IONS

(75) Inventors: Markus Schubert, Ludwigshafen (DE); Ulrich Mueller, Neustadt (DE); Markus Tonigold, Blaustein (DE); Roger Ruetz, Mannheim (DE)

(73) Assignee: BASF SE, Ludwigshafen (DE)

( * ) Notice: Subject to any disclaimer, the term of this patent is extended or adjusted under 35 U.S.C. 154(b) by 1097 days.

(21) Appl. No.: 12/063,522

(22) PCT Filed: Aug. 18, 2006

(86) PCT No.: PCT/EP2006/065442
§ 371 (c)(1),
(2), (4) Date: Feb. 11, 2008

(87) PCT Pub. No.: WO2007/023134
PCT Pub. Date: Mar. 1, 2007

(65) Prior Publication Data
US 2010/0166644 A1    Jul. 1, 2010

(30) Foreign Application Priority Data
Aug. 22, 2005   (DE) .................. 10 2005 039 623

(51) Int. Cl.
*C01B 3/00*   (2006.01)
*B01D 53/02*  (2006.01)
(Continued)

(52) U.S. Cl.
CPC ............ *C01B 3/0026* (2013.01); *B01D 53/02* (2013.01); *B01J 20/226* (2013.01);
(Continued)

(58) Field of Classification Search
CPC .................................................... C01B 3/0026
See application file for complete search history.

(56) References Cited

U.S. PATENT DOCUMENTS 5,648,508 A * 7/1997 Yaghi ................. 556/9
7,119,219 B2  10/2006 Mueller et al.

FOREIGN PATENT DOCUMENTS

DE        10111230     9/2002
EP         0790253     8/1997
(Continued)

OTHER PUBLICATIONS

Zhang et al, new double layered open metal organic frameworks with nanosized channels encapsulated removable 2, 5-bis-(4-pyridyl)-1, 3, 4-thiadiazole molecules, 2005, crystengcomm, vol. 7 pp. 96-101.*

(Continued)

*Primary Examiner* — Melvin C Mayes
*Assistant Examiner* — Stefanie Cohen
(74) *Attorney, Agent, or Firm* — Oblon, McClelland, Maier & Neustadt, L.L.P.

(57) ABSTRACT

The present invention relates to a process for preparing a porous metal-organic framework by reacting at least one metal compound in which the metal is Be, Mg, Ca, Sr, Ba, Al, Ga or In with at least one at least bidentate organic compound and also the use of such porous metal-organic frameworks.

17 Claims, 9 Drawing Sheets

(51) Int. Cl.
*B01J 20/22* (2006.01)
*B01J 20/28* (2006.01)
*B01J 31/16* (2006.01)
*B01J 31/18* (2006.01)
*B01J 31/22* (2006.01)
*C07C 51/41* (2006.01)
*C07F 5/06* (2006.01)
*F17C 11/00* (2006.01)

(52) U.S. Cl.
CPC ... *B01J 20/28014* (2013.01); *B01J 20/28057* (2013.01); *B01J 31/1691* (2013.01); *B01J 31/1805* (2013.01); *B01J 31/226* (2013.01); *B01J 31/2239* (2013.01); *C07C 51/418* (2013.01); *C07F 5/069* (2013.01); *F17C 11/007* (2013.01); *B01D 2253/204* (2013.01); *B01J 2231/12* (2013.01); *B01J 2231/20* (2013.01); *B01J 2531/21* (2013.01); *B01J 2531/22* (2013.01); *B01J 2531/23* (2013.01); *B01J 2531/25* (2013.01); *B01J 2531/31* (2013.01); *B01J 2531/32* (2013.01); *B01J 2531/33* (2013.01); *Y02E 60/321* (2013.01); *Y02E 60/327* (2013.01)

(56) References Cited

FOREIGN PATENT DOCUMENTS

| JP | 59155333 | | 9/1984 |
|----|----------|---|--------|
| WO | WO2004042270 | * | 5/2004 |
| WO | WO 2005/049892 A1 | | 6/2005 |

OTHER PUBLICATIONS

Huang et al, synthesis, morphology control, and properties of porous metal organic coordination polymers, 2003, microporous and mesoporous materials, 58 pgs, 105-114.*

Huang et al, Synthesis, morphology control, and properties of porous metal-organic coordination polymers, 2003, microporous and mesoporous materials, vol. 58, issue 2, pp. 105-114.*

U.S. Appl. No. 12/668,436, filed Jan. 11, 2010, Schubert, et al.

M.O. Keeffe, et al. "Frameworks for Extended Solids: Geometrical Design Principles" Journal of Solid State Chemistry, vol. 152, pp. 3-20, (2000).

H. Li, et al. "Design and synthesis of an Exceptionally Stable and Highly Porous Metal-Organic Framework" Nature, vol. 402, pp. 276-279, (Nov. 1999).

M. Eddaoudi, et al. "Design and synthesis of Metal-Carboxylate Frameworks with Permanent Microporosity" Topics in Catalysis, vol. 9, pp. 105-111, (1999).

B. Chen, et al. "Interwoven Metal-Organic Framework on a Periodic Minimal Surface with Extra-Large Pores" Science, vol. 291, pp. 1021-1023, (Feb. 2001).

T. Loiseau, et al. "A Rationale for the Large Breathing of the Porous Aluminum Terephthalate (MIL-53) Upon Hydration" Chem. Eur. J., vol. 10, pp. 1373-1382, (2004).

Z. Lin, et al. "New 3-D Chiral Framework of Indium with 1,3,5-Benzenetricarboxylate" Inorganic Chemistry, vol. 44, pp. 73-76, (2005).

L. Pan, et al. "The Effect of pH on the Dimensionality of Coordination Polymers" Inorg. Chem, vol. 40, pp. 1271-1283, (2001).

Z. Fei, et al. "A Nearly Planar Water Sheet Sandwiched Between Strontium-Imidazolium Carboxylate coordination Polymers" Inorg. Chem, vol. 44, No. 15, pp. 5200-5202, (2005).

H. F. Zhu, et al. "Syntheses, Structures, and Properties of Two-Dimensional Alkaline Earth Metal Complexes with Flexible Tripodal Tricarboxylate Ligands" Crystal Growth and Design, vol. 5, No. 1, pp. 177-182, (2005).

J. Sun, et al. "QMOF-1 and QMOF-2: Three-Dimensional Metal-Organic Open Frameworks with a Quartzlike Topology" Angew. Chem, vol. 114, No. 23, pp. 4651-4653, (2002).

B. Gomez-Lor, et al. "In2(OH)3(BDC)1.5 (BDC=1,4-Benzendicarboxylate): An In(III) Supramolecular 3D Framework with Catalytic Activity" Inorg. Chem, vol. 41, 2429-2432 (2002).

U.S. Appl. No. 12/594,604, filed Oct. 5, 2009, Stein, et al.
U.S. Appl. No. 12/597,616, filed Oct. 26, 2009, Schubert, et al.
U.S. Appl. No. 12/601,022, filed Nov. 20, 2009, Schubert, et al.
U.S. Appl. No. 12/600,539, filed Nov. 17, 2009, Schubert, et al.

Xuebo Zhao, et al. "Hysteretic Adsorption and Desorption of Hydrogen by Nanoporous Metal-Organic Frameworks", Science, vol. 306, Nov. 5, 2004, pp. 1012-1015 (with cover page).

* cited by examiner

METHOD FOR PRODUCING ORGANOMETALLIC FRAMEWORK MATERIALS CONTAINING MAIN GROUP METAL IONS

This application is a 371 of PCT/EP06/065442, filed Aug. 18, 2006.

DESCRIPTION

Figure 1:
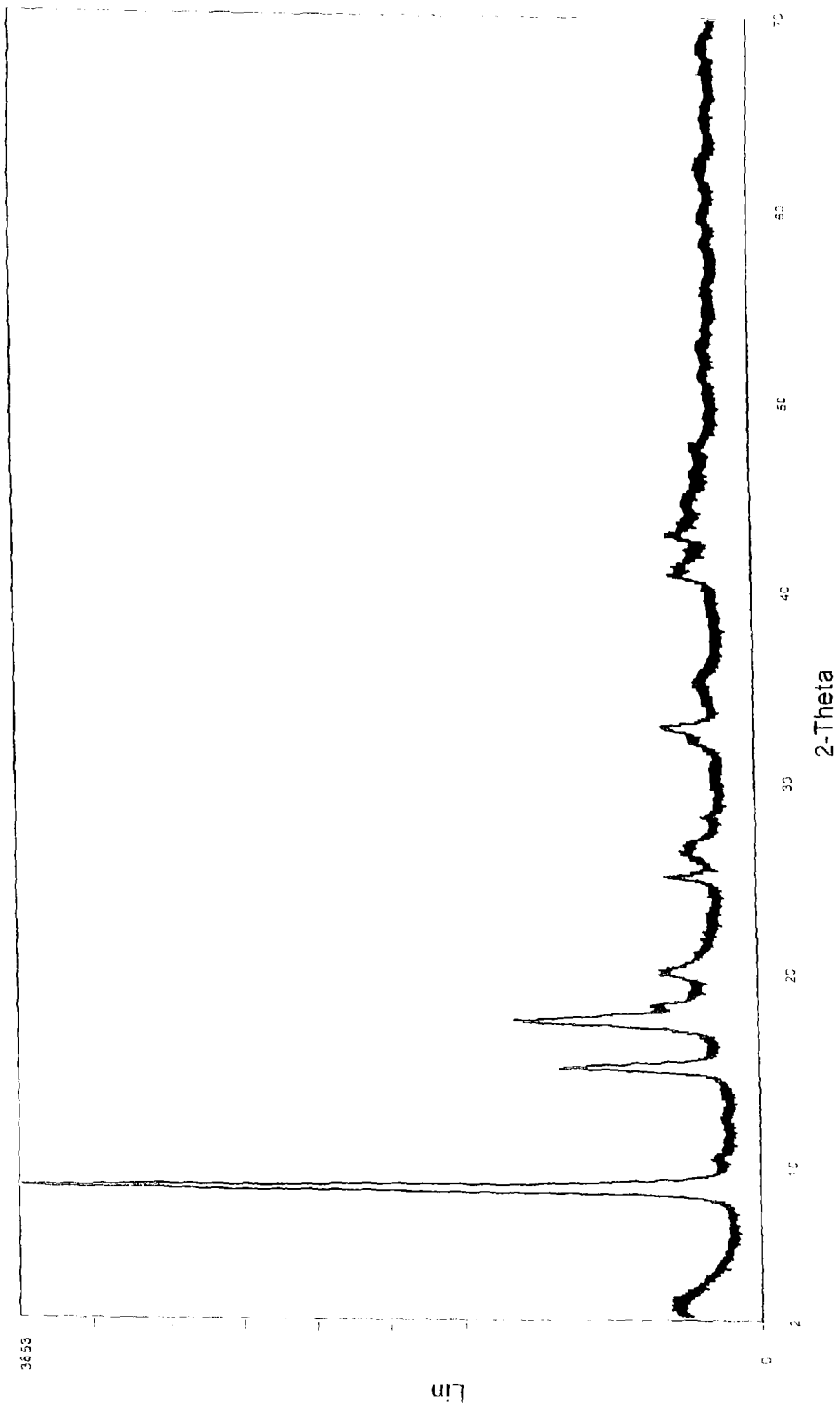
FIG. 1 The diffraction pattern (XRD) of Example 1.

The present invention relates to a process for preparing a porous metal-organic framework and the use of the frameworks prepared.

Porous metal-organic frameworks are known from the prior art. These typically comprise at least one at least bidentate organic compound coordinated to at least one metal ion. Such metal-organic frameworks (MOFs) are described, for example, in U.S. Pat. No. 5,648,508, EP-A 0 790 253, M. O. Keeffe, J. Sol. State Chem., 152 (2000), 3-20; H. Li et al., Nature 402 (1999), 276; M. Eddaoudi, Topics in catalysis 9 (1999), 105-111; B. Chen et al., Science 291 (2001), 1021-1023 and DE-A 101 11 230.

Numerous processes for preparing such porous metal-organic frameworks have been developed. Typically, a metal salt is reacted with the at least bidentate organic compound, for example a dicarboxylic acid, in a suitable solvent under superatmospheric pressure and at elevated temperature.

However, difficulties frequently occur here. A problem can be that, as a result of the use of a metal salt, the counterion to the metal cation (for example nitrate) which remains in the reaction medium after formation of the metal-organic framework has to be separated off from the framework.

The use of high pressures and temperatures places severe demands on the apparatus used for synthesizing a porous metal-organic framework. Usually only a batch synthesis in comparatively small apparatuses is possible and has been described. A scale-up proves to be very expensive.

A further difficulty is that, depending on the metal and organic compound used for preparing the framework, the reaction conditions cannot readily be carried over. This is the case, for example, when the metal component in the metal-organic framework is a main group metal of the second or third main group of the Periodic Table. Here, the reaction conditions employed for the preparation are sometimes significantly different from those for analogous frameworks in which the metal component is a transition metal, for example zinc or copper.

Such porous metal-organic frameworks which can comprise a main group metal of the second or third main group also differ from the abovementioned analogous frameworks in terms of their properties, which could be a reason for modified preparative methods frequently being employed in the prior art for their preparation.

T. Loiseau et al., Chem. Eur. J. 2004, (10), 1373-1382, describe, for example, the preparation of porous aluminum terephthalate. This has a remarkably high thermal stability. Thus, it is reported that the material decomposes only at a temperature above 500° C. The synthesis is carried out by reaction of aluminum nitrate (as nonahydrate) and 1,4-benzenedicarboxylic acid in deionized water. The reaction is carried out under superatmospheric pressure at 220° C. In contrast to other metal-organic frameworks, it is found that the ligand used as organic compound in the preparation not only appears as framework building block in the metal-organic framework but is also retained as ligand in the pores of the framework. This additional binding of the ligand in the porous metal-organic framework typically does not occur in the case of analogous frameworks which are derived from transition metals. To solve this problem, Loiseau et al. suggest heating the material until the ligand trapped in the pores is removed. This procedure has the disadvantage that the actual synthesis has to be followed by a sometimes time-consuming and stringent after-treatment step which is strongly dependent on the boiling point or vapor pressure of the ligand. In the case of particularly high-boiling ligands, this procedure can also fail completely.

Z. Lin et al., Inorganic Chemistry 44 (2005), 73-76, describe a metal-organic framework in which indium forms the metal component and 1,3,5-benzenetricarboxylic acid is used as organic compound. Water is likewise used as solvent here. Furthermore, Lin et al. indicate that a high excess of a base (pyridine) has to be added to the reaction in order to set an adequate pH.

L. Pan et al., Inorg. Chem. 40 (2001), 1271-1283, describe calcium-, strontium- and barium-comprising porous metal-organic frameworks and likewise propose the use of water or water/triethylamine. 3,5-Pyrazoledicarboxylic acid is used as ligand.

Z. Fei et al., Inorg. Chem. 44 (2005), 5200-5202, describe strontium-imidazolium carboxylates.

H.-F. Zhu et al., Crystal Growth & Design 5 (2005), 177-182, describe metal-organic frameworks derived from calcium and barium together with 1,3,5-benzenetricarboxylic acid in water.

J. Sun et al., Angew. Chem. 114 (2002), 4651-4653, describe, inter alia, the preparation of indium terephthalate in DMF. Here, the reaction takes place under superatmospheric pressure at 160° C.

B. Gomez-Lor et al., Inorganic Chemistry 41 (2002), 2429-2432, likewise describe indium terephthalate, with the reaction being carried out in water using triethylamine as base.

Disadvantages of the use of water are the sometimes poor solubility of the organic compound in water and the low yields of framework which are frequently obtained and/or its low specific surface area.

A further disadvantage is the use of high pressures. Here, the difficulty of constructing the apparatus usually does not allow stirring for mixing the individual starting materials for preparing the metal-organic framework.

There is thus still a need for improved processes for preparing porous metal-organic frameworks in which the metal component is a metal of the second or third main group of the Periodic Table.

It is therefore an object of the present invention to provide an improved process for preparing such porous metal-organic frameworks.

This object is achieved by a process for preparing a porous metal-organic framework, which comprises the step reaction of at least one metal compound with at least one at least bidentate organic compound which can coordinate to the metal, in the presence of a nonaqueous organic solvent, where the metal is $Be^{II}$, $Mg^{II}$, $Ca^{II}$, $Sr^{II}$, $Ba^{II}$, $Al^{III}$, $Ga^{III}$ or $In^{III}$ and the organic compound has at least two atoms which are selected independently from the group consisting of oxygen, sulfur and nitrogen and via which the organic compound can coordinate to the metal, with the reaction being carried out with stirring and at a pressure of not more than 2 bar (absolute).

It has been found that the use of a nonaqueous organic solvent and the further conditions mentioned make it possible to achieve an at least partially more efficient preparation of a porous metal-organic framework which, in particular, makes simple scale-up possible.

An advantage is, inter alia, that the reaction can take place with stirring, which is also advantageous for scale-up.

The reaction is carried out at a pressure of not more than 2 bar (absolute). However, the pressure is preferably not more than 1230 mbar (absolute). The reaction very particularly preferably takes place at atmospheric pressure.

The reaction can be carried out at room temperature. However, it preferably takes place at temperatures above room temperature. The temperature is preferably more than 100° C. Furthermore, the temperature is preferably not more than 180° C. and more preferably not more than 150° C.

The above-described metal-organic frameworks are typically prepared in water as solvent with addition of a further base. The latter serves, in particular, to make a polybasic carboxylic acid used as at least bidentate organic compound readily soluble in water. As a result of the use of the nonaqueous organic solvent, it is not necessary to use such a base. Nonetheless, the solvent for the process of the invention can be selected so that it has a basic reaction, but this is not absolutely necessary for carrying out the process of the invention.

It is likewise possible to use a base. However, preference is given to using no additional base.

Furthermore, the metal compound used for preparing the porous metal-organic framework can preferably be nonionic and/or the counterion to the metal cation can be derived from a protic solvent. The use of an appropriate nonionic compound makes it possible to avoid the presence of a metal salt in the reaction to form the porous metal-organic framework, which could result in difficulties in the removal of the corresponding anion of the metal salt, as long as no further interfering salts are produced by the metal compound in the reaction. If the counterion is a solvent anion, this can, when chosen appropriately, be present as solvent after the reaction. This solvent can be the same as the nonaqueous organic solvent used or be different therefrom. In the latter case, preference is given to this solvent being at least partly miscible with the nonaqueous organic solvent. If water is formed in the reaction of the metal compound, its proportion should be within the limits described further below. This can be achieved by using a sufficient amount of the nonaqueous organic solvent.

Nonionic compounds or counterions to the metal cation which can be derived from protic solvents can be, for example, metal alkoxides, for example methoxides, ethoxides, propoxides, butoxides, in particular aluminum alkoxides. Oxides or hydroxides are likewise conceivable.

The metal used is $Be^{II}$, $Mg^{II}$, $Ca^{II}$, $Sr^{II}$, $Ba^{II}$, $Al^{III}$, $Ga^{III}$ or $In^{III}$. The metal is preferably $Mg^{II}$, $Ca^{II}$, $Sr^{II}$, $Ba^{II}$, $Al^{III}$ or $In^{III}$. Very particular preference is given to $Al^{III}$ and $Mg^{II}$. $Al^{III}$ is especially preferred.

The at least one at least bidentate organic compound has at least two atoms which are selected independently from the group consisting of oxygen, sulfur and nitrogen and via which the organic compound can coordinate to the metal. These atoms can be part of the skeleton or be functional groups.

As functional groups via which the abovementioned coordinate bonds can be formed, mention may be made by way of example of, in particular, the following functional groups: $-CO_2H$, $-CS_2H$, $-COSH$, $-NO_2$, $-SO_3H$, $-Ge(OH)_3$, $-Sn(OH)_3$, $-Si(SH)_4$, $-Ge(SH)_4$, $-Sn(SH)_3$, $-AsO_3H$, $-AsO_4H$, $-P(SH)_3$, $-As(SH)_3$, $-CH(RSH)_2$, $-C(RSH)_3$, $-CH(RNH_2)_2$, $-C(RNH_2)_3$, $-CH(ROH)_2$, $-C(ROH)_3$, $-CH(RCN)_2$, $-C(RCN)_3$, where R is preferably, for example, an alkylene group having 1, 2, 3, 4 or 5 carbon atoms, for example a methylene, ethylene, n-propylene, i-propylene, n-butylene, i-butylene, tert-butylene or n-pentylene group, or an aryl group comprising 1 or 2 aromatic rings, for example 2 $C_6$ rings, which may, if appropriate, be fused and be appropriately substituted, independently of one another, by at least one substituent each and/or may comprise, independently of one another, at least one heteroatom such as N, O and/or S. According to likewise preferred embodiments, mention may be made of functional groups in which the abovementioned radical R is not present. In this respect, mention may be made of, inter alia, $-CH(SH)_2$, $-C(SH)_3$, $-CH(NH_2)_2$, $-C(NH_2)_3$, $-CH(OH)_3$, $-CH(CN)_2$ or $-C(CN)_3$.

The at least two functional groups can in principle be bound to any suitable organic compound as long as it is ensured that the organic compound bearing these functional groups is capable of forming the coordinate bond and is suitable for the preparation of the framework.

The organic compounds comprising at least two functional groups are preferably derived from a saturated or unsaturated aliphatic compound or an aromatic compound or a both aliphatic and aromatic compound.

The aliphatic compound or the aliphatic part of the both aliphatic and aromatic compound can be linear and/or branched and/or cyclic, with a plurality of rings per compound also being possible. More preferably, the aliphatic compound or the aliphatic part of the both aliphatic and aromatic compound comprises from 1 to 15, more preferably from 1 to 14, more preferably from 1 to 13, more preferably from 1 to 12, more preferably from 1 to 11 and particularly preferably from 1 to 10, carbon atoms, for example, 1, 2, 3, 4, 5, 6, 7, 8, 9 or 10 carbon atoms. Particular preference is here given to, inter alia, methane, ethane, butane, 2-butene, adamantane, acetylene, ethylene or butadiene.

The aromatic compound or the aromatic part of the both aromatic and aliphatic compound can have one or more rings, for example two, three, four or five rings, in which case the rings may be present separately from one another and/or at least two rings may be present in fused form. The aromatic compound or the aromatic part of the both aliphatic and aromatic compound more preferably has one, two or three rings, with one or two rings being particularly preferred. Furthermore, each ring of the compound mentioned can independently comprise at least one heteroatom such as N, O, S, B, P, Si, preferably N, O and/or S. More preferably, the aromatic compound or the aromatic part of the both aromatic and aliphatic compound comprises one or two $C_6$ rings, with the two being able to be present separately from one another or in fused form. In particular, mention may be made of benzene, pyrene, dihydropyrene, naphthalene and/or biphenyl and/or bipyridyl and/or pyridine as aromatic compounds.

Examples which may be mentioned are, inter alia, transmuconic acid and fumaric acid and phenylenebisacrylic acid.

For the purposes of the present invention, mention may be made, for example of dicarboxylic acids such as oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxylic acid, heptadecanedicarboxylic acid, acetylenedicarboxylic acid, 1,2-benzenedicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxylic acid, 2-methylquinoline-3,4-dicarboxylic acid, quinoline-2,4-dicarboxylic acid, quinoxaline-2,3-dicarboxylic acid, 6-chloro-quinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropylimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octanedicarboxylic acid, pentane-3,3-dicarboxylic acid, 4,4'-diamino-1,1'-diphenyl-3,3'-dicarboxylic acid, 4,4'-diaminodiphenyl-3,3'-dicarboxylic acid, benzidine-3,3'-dicarboxylic acid, 1,4-bis(phenylamino)benzene-2,5-dicarboxylic acid, 1,1'-binaphthyldicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyrazole-3,4-dicarboxylic acid, 2,3-pyrazinedicarboxylic acid, 5,6-dimethyl-2,3-pyrazinedicarboxylic acid, 4,4'-diamino(diphenyl ether)diimidedicarboxylic acid, 4,4'-diaminodiphenylmethanediimidedicarboxylic acid, 4,4'-diamino(diphenyl sulfone)-diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4''-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexene-1,2-dicarboxylic acid, hexatriacontanedicarboxylic acid, tetradecanedicarboxylic acid, 1,7-heptanedicarboxylic acid, 5-hydroxy-1,3-benzenedicarboxylic acid, 2,5-dihydroxy-1,4-dicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxy-diphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid 1,14-tetradecanedicarboxylic acid, 5,6-dehydronorbornane-2,3-dicarboxylic acid, 5-ethyl-2,3-pyridinedicarboxylic acid or camphordicarboxylic acid, tricarboxylic acids such as 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurintricarboxylic acid, or tetracarboxylic acids such as 1,1-dioxidoperylo[1,12-BCD]thiophene-3,4,9,10-tetracarboxylic acid, perylene-tetracarboxylic acids such as perylene-3,4,9,10-tetracarboxylic acid or perylene-1,12-sulfone-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octane-tetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.

Very particular preference is given to using unsubstituted or optionally at least monosubstituted aromatic dicarboxylic, tricarboxylic or tetracarboxylic acids having one, two, three, four or more rings, with each of the rings being able to comprise at least one heteroatom and two or more rings being able to comprise identical or different heteroatoms. Examples of preferred carboxylic acids of this type are one-ring dicarboxylic acids, one-ring tricarboxylic acids, one-ring tetracarboxylic acids, two-ring dicarboxylic acids, two-ring tricarboxylic acids, two-ring tetracarboxylic acids, three-ring dicarboxylic acids, three-ring tricarboxylic acids, three-ring tetracarboxylic acids, four-ring dicarboxylic acids, four-ring tricarboxylic acids and/or four-ring tetracarboxylic acids. Suitable heteroatoms are, for example, N, O, S, B, P, Si, and preferred heteroatoms are N, S and/or O.

Suitable substituents are, inter alia, —OH, a nitro group, an amino group or an alkyl or alkoxy group.

As at least bidentate organic compounds particular preference is given to using acetylenedicarboxylic acid (ADC), camphordicarboxylic acid, fumaric acid, succinic acid, benzenedicarboxylic acids, naphthalenedicarboxylic acids, biphenyldicarboxylic acids such as 4,4'-biphenyldicarboxylic acid (BPDC), pyrazinedicarboxylic acids, such as 2,5-pyrazinedicarboxylic acid, bipyridinedicarboxylic acids such as 2,2'-bipyridinedicarboxylic acids, e.g. 2,2'-bipyridine-5,5'-dicarboxylic acid, benzenetricarboxylic acids such as 1,2,3-, 1,2,4-benzenetricarboxylic acid or 1,3,5-benzenetricarboxylic acid (BTC), benzenetetracarboxylic acid, adamantanetetracarboxylic acid (ATC), adamantanedibenzoate (ADB), benzenetribenzoate (BTB), methanetetrabenzoate (MTB), adamantanetetrabenzoate or dihydroxyterephthalic acids such as 2,5-dihydroxyterephthalic acid (DHBDC).

Very particular preference is given to using, inter alia, isophthalic acid, terephthalic acid, 2,5-dihydroxyterephthalic acid, 1,2,3-benzenetricarboxylic acid, 1,3,5-benzenetricarboxylic acid, 2,6-naphthalenedicarboxylic acid, 1,4-naphthalenedicarboxylic acid, 1,2,3,4- and 1,2,4,5-benzenetetracarboxylic acid, camphordicarboxylic acid or 2,2'-bipyridine-5,5'-dicarboxylic acid.

Apart from these at least bidentate organic compounds, the metal-organic framework can further comprise one or more monodentate ligands.

The at least one at least bidentate organic compound preferably comprises no boron or phosphorus atoms. Furthermore, the skeleton of the metal-organic framework preferably comprises no boron or phosphorus atoms.

The nonaqueous organic solvent is preferably a $C_{1-6}$-alkanol, dimethyl sulfoxide (DMSO), N,N-dimethylformamide (DMF), N,N-diethylformamide (DEF), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone, sulfolene or a mixture thereof.

A $C_{1-6}$-alkanol is an alcohol having from 1 to 6 carbon atoms. Examples are methanol, ethanol, n-propanol, i-propanol, n-butanol, i-butanol, t-butanol, pentanol, hexanol and mixtures thereof.

An optionally halogenated $C_{1-200}$-alkane is an alkane having from 1 to 200 carbon atoms in which one or more up to all hydrogen atoms may be replaced by halogen, preferably chlorine or fluorine, in particular chlorine. Examples are chloroform, dichloromethane, tetrachloromethane, dichloroethane, hexane, heptane, octane and mixtures thereof.

Preferred solvents are DMF, DEF and NMP. Particular preference is given to DMF.

The term "nonaqueous" preferably refers to a solvent which has a maximum water content of 10% by weight, more preferably 5% by weight, even more preferably 1% by weight, still more preferably 0.1% by weight, particularly preferably 0.01% by weight, based on the total weight of the solvent.

The maximum water content during the reaction is preferably 10% by weight, more preferably 5% by weight and even more preferably 1% by weight.

The term "solvent" encompasses pure solvents and mixtures of various solvents.

Furthermore, the process step of reaction of the at least one metal compound with the at least one at least bidentate organic compound is preferably followed by a calcination step. The temperature set here is typically above 250° C., preferably from 300 to 400° C.

The calcination step can, in particular, remove the ligand present in the pores in the preparation of porous aluminum frameworks.

In addition or as an alternative thereto, the removal of ligand from the pores of the porous metal-organic framework can be effected by treatment of the framework formed with a nonaqueous solvent. Here, the ligand is removed in the manner of an "extraction process" and, if appropriate, replaced in the framework by a solvent molecule. This mild method is particularly useful when the ligand is a high-boiling compound.

The treatment is preferably carried out for at least 30 minutes and can typically be carried out for up to 2 days. This can occur at room temperature or elevated temperature. It is preferably carried out at elevated temperature, for example at at least 40° C., preferably 60° C. Further preference is given to the extraction taking place at the boiling point of the solvent used (under reflux).

The treatment can be carried out in a simple vessel by slurrying and stirring the framework. It is also possible to use extraction apparatuses such as Soxhlet apparatuses, in particular industrial extraction apparatuses.

Suitable solvents are those mentioned above, i.e., for example, $C_{1-6}$-alkanol, dimethyl sulfoxide (DMSO), N,N-dimethylformamide (DMF), N,N-diethylformamide (DEF), acetonitrile, toluene, dioxane, benzene, chlorobenzene, methyl ethyl ketone (MEK), pyridine, tetrahydrofuran (THF), ethyl acetate, optionally halogenated $C_{1-200}$-alkane, sulfolane, glycol, N-methylpyrrolidone (NMP), gamma-butyrolactone, alicyclic alcohols such as cyclohexanol, ketones such as acetone or acetylacetone, cyclic ketones such as cyclohexanone or mixtures thereof.

Preference is given to methanol, ethanol, propanol, acetone, MEK and mixtures thereof.

A very particularly preferred extractant is methanol.

The solvent used for extraction can be identical to or different from that used for the reaction of the at least one metal compound with the at least one at least bidentate organic compound. In particular, it is not absolutely necessary but is preferred that the solvent used in the "extraction" is water-free.

The metal-organic frameworks of the present invention comprise pores, in particular micropores and/or mesopores. Micropores are defined as pores having a diameter of 2 nm or less and mesopores are defined by a diameter in the range from 2 to 50 nm, in each case corresponding to the definition given in Pure Applied Chem. 57 (1985), pages 603-619, in particular on page 606. The presence of micropores and/or mesopores can be checked with the aid of sorption measurements, with these measurements determining the uptake capacity of the MOF for nitrogen at 77 kelvin in accordance with DIN 66131 and/or DIN 66134.

The specific surface area calculated by the Langmuir model in accordance with DIN 66135 (DIN 66131, 66134) of a metal-organic framework in powder form is preferably greater than 5 $m^2/g$, more preferably above 10 $m^2/g$, more preferably greater than 50 $m^2/g$, even more preferably greater than 500 $m^2/g$, even more preferably greater than 1000 $m^2/g$ and particularly preferably greater than 1250 $m^2/g$.

Shaped MOF bodies can have a lower specific surface area; however, this is preferably greater than 10 $m^2/g$, more preferably greater than 50 $m^2/g$, even more preferably greater than 500 $m^2/g$.

The pore size of the metal-organic framework can be controlled by selection of the suitable ligand and/or the at least bidentate organic compound. It is frequently the case that the larger the organic compound, the larger the pore size. The pore size is preferably from 0.2 nm to 30 nm, particularly preferably in the range from 0.3 nm to 9 nm, based on the crystalline material.

However, larger pores whose size distribution can vary also occur in a shaped MOF body. However, preference is given to more than 50% of the total pore volume, in particular more than 75%, being formed by pores having a pore diameter of up to 1000 nm. However, a major part of the pore volume is preferably formed by pores in two diameter ranges. It is therefore further preferred that more than 25% of the total pore volume, in particular more than 50% of the total pore volume, is formed by pores in a diameter range from 100 nm to 800 nm and more than 15% of the total pore volume, in particular more than 25% of the total pore volume, is formed by pores in a diameter range up to 10 nm. The pore size distribution can be determined by means of mercury porosimetry.

The metal-organic framework can be in powder form or be present as agglomerates. The framework can be used as such or it is converted into a shaped body. Preferred processes are extrusion or tableting. In the production of shaped bodies, the framework can comprise further materials such as binders, lubricants or other additives which are added during the production process. It is likewise conceivable for the framework to comprise further constituents such as adsorbents such as activated carbon or the like.

The possible geometries of these shaped bodies are subject to essentially no restrictions. Examples are, inter alia, pellets such as disk-shaped pellets, pills, spheres, granules, extrudates such as rod extrudates, honeycombs, grids and hollow bodies.

All suitable processes are in principle possible for producing these shaped bodies. In particular, the following processes, inter alia, are preferred:
  kneading of the framework either alone or together with at least one binder and/or at least one pasting agent and/or at least one template compound to give a mixture; shaping of the resulting mixture by means of at least one suitable method, for example extrusion; optionally washing and/or drying and/or calcination of the extrudate; optionally finishing.
  Application of the framework to at least one optionally porous support material. The material obtained can then be processed further by the method described above to give a shaped body.
  Application of the framework to at least one optionally porous substrate.

Kneading and shaping can be carried out by any suitable method, as described, for example, in Ullmanns Enzyklopadie der Technischen Chemie, 4th edition, Volume 2, p. 313 ff. (1972).

For example, the kneading and/or shaping can preferably be carried out by means of a piston press, roll press in the presence or absence of at least one binder material, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or at elevated pressure, for example in the range from atmospheric pressure to a few hundred bar, and/or in a protective gas atmosphere, for example in the presence of at least one noble gas, nitrogen or a mixture of two or more thereof.

The kneading and/or shaping is, according to a further embodiment, carried out with addition of at least one binder, with the binder used being able in principle to be any chemical compound which ensures the desired viscosity for kneading and/or shaping the composition. Accordingly, binders can, for the purposes of the present invention, be either viscosity-increasing or viscosity-reducing compounds.

Preferred binders include, for example, aluminum oxide or binders comprising aluminum oxide as described, for example, in WO 94/29408, silicon dioxide as described, for example, in EP 0 592 050 A1, mixtures of silicon dioxide and aluminum oxide as described, for example, in WO 94/13584, clay minerals as described, for example, in JP 03-037156 A, for example montmorillonite, kaolin, bentonite, hallosite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, and, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, and, for example, trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, and, for example, trialkoxyzirconates such as trimethoxyzirconate, triethoxyzirconate, tripropoxyzirconate, tributoxyzirconate, silica sols, amphiphilic substances and/or graphites. Particular preference is given to graphite.

As viscosity-increasing compound, it is also possible, for example, to use, if appropriate in addition to the abovementioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran or a polyethylene oxide.

As pasting agent, preference is given to using, inter alia, water or at least one alcohol, for example a monoalcohol having from 1 to 4 carbon atoms, e.g. methanol, ethanol, n-propanol, isopropanol, 1-butanol, 2-butanol, 2-methyl-1-propanol or 2-methyl-2-propanol, or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222.

The order of addition of the additives such as template compound, binder, pasting agent, viscosity-increasing substance in shaping and kneading is in principle not critical.

In a further preferred embodiment, the shaped body obtained by kneading and/or shaping is subjected to at least one drying operation which is generally carried out at a temperature in the range from 25 to 300° C., preferably in the range from 50 to 300° C. and particularly preferably in the range from 100 to 300° C. It is likewise possible to carry out drying under reduced pressure or under a protective gas atmosphere or by spray drying.

In a particularly preferred embodiment, at least one of the compounds added as additives is at least partly removed from the shaped body during this drying operation.

The present invention further provides a porous metal-organic framework obtainable by a process according to the invention for its preparation. Here, the framework preferably has the specific surface areas (determined by the Langmuir method) indicated above in general terms for frameworks.

The present invention further provides for the use of a porous metal-organic framework comprising at least one metal selected from the group consisting of $Be^{II}$, $Mg^{II}$, $Ca^{II}$, $Sr^{II}$, $Ba^{II}$, $Al^{III}$, $Ga^{III}$ and $In^{III}$ and at least one at least bidentate organic compound, where the organic compound has at least two atoms which are selected independently from the group consisting of oxygen, sulfur and nitrogen and via which the organic compound coordinates to the metal, in particular a framework obtainable by the process of the invention, for the uptake of at least one substance for the purposes of its storage, separation, controlled release or chemical reaction and also as support material, for example for metals, metal oxides, metal sulfides or other framework structures.

The at least one substance can be a gas or a liquid. The substance is preferably a gas.

For the purposes of the present invention, the terms "gas" and "liquid" are used in the interests of simplicity, but gas mixtures and liquid mixtures or liquid solutions are likewise encompassed by the term "gas" or "liquid".

Preferred gases are hydrogen, hydrocarbons, in particular methane, ethane, ethene, acetylene, propane, n-butane and i-butane, carbon monoxide, carbon dioxide, nitrogen oxides, oxygen, sulfur oxides, halogens, halogenated hydrocarbons, $NF_3$, $SF_6$, ammonia, boranes, phosphanes, hydrogen sulfide, amines, formaldehyde, noble gases, in particular helium, neon, argon, krypton and xenon.

Particular preference is given to the use of a metal-organic framework according to the invention in which the metal is $Al^{III}$ or $Mg^{II}$ for the storage of hydrogen.

However, the at least one substance can also be a liquid. Examples of such liquids are disinfectants, inorganic or organic solvents, fuels, in particular gasoline or diesel, hydraulic fluids, radiator fluids, brake fluids or an oil, in particular machine oil. Furthermore, the liquid can also be a halogenated aliphatic or aromatic, cyclic or acyclic hydrocarbon or a mixture thereof. In particular, the liquid can be acetone, acetonitrile, aniline, anisole, benzene, benzonitrile, bromobenzene, butanol, tert-butanol, quinoline, chlorobenzene, chloroform, cyclohexane, diethylene glycol, diethyl ether, di methylacetamide, dimethylformamide, dimethyl sulfoxide, dioxane, glacial acetic acid, acetic anhydride, ethyl acetate, ethanol, ethylene carbonate, ethylene dichloride, ethylene glycol, ethylene glycol dimethyl ether, formamide, hexane, isopropanol, methanol, methoxypropanol, 3-methyl-1-butanol, methylene chloride, methyl ethyl ketone, N-methylformamide, N-methylpyrrolidone, nitrobenzene, nitromethane, piperidine, propanol, propylene carbonate, pyridine, carbon disulfide, sulfolane, tetrachloroethene, carbon tetrachloride, tetrahydrofuran, toluene, 1,1,1-trichloroethane, trichloroethylene, triethylamine, triethylene glycol, triglyme, water or a mixture thereof.

The at least one substance can also be an odorous substance.

The odorous substance is preferably a volatile organic or inorganic compound which comprises at least one of the elements nitrogen, phosphorous, oxygen, sulfur, fluorine, chlorine, bromine or iodine or is an unsaturated or aromatic hydrocarbon or a saturated or unsaturated aldehyde or a ketone. More preferred elements are nitrogen, oxygen, phosphorous, sulfur, chlorine, bromine; and particular preference is given to nitrogen, oxygen, phosphorous and sulfur.

In particular, the odorous substance is ammonia, hydrogen sulfide, sulfur oxides, nitrogen oxides, ozone, cyclic or acyclic amines, thiols, thioethers and also aldehydes, ketones, esters, ethers, acids or alcohols. Particular preference is given to ammonia, hydrogen sulfide, organic acids (preferably acetic acid, propionic acid, butyric acid, isobutyric acid, valeric acid, isovaleric acid, caproic acid, heptanoic acid, lauric acid, pelargonic acid) and cyclic or acyclic hydrocarbons which comprise nitrogen or sulfur and also saturated or unsaturated aldehydes such as hexanal, heptanal, octanal, nonanal, decanal, octenal or nonenal and in particular volatile aldehydes such as butyraldehyde, propionaldehyde, acetaldehyde and formaldehyde and also fuels such as gasoline, diesel (constituents).

The odorous substances can also be fragrances which are used, for example, for producing perfumes. Examples of fragrances or oils which release such fragrances are: essential oils, basil oil, geranium oil, mint oil, cananga oil, cardamom oil, lavender oil, peppermint oil, nutmeg oil, camomile oil, eucalyptus oil, rosemary oil, lemon oil, lime oil, orange oil, bergamot oil, muscatel sage oil, coriander oil, cypress oil, 1,1-dimethoxy-2-phenylethane, 2,4-dimethyl-4-phenyltetrahydrofuran, dimethyltetrahydrobenzaldehyde, 2,6-dimethyl-7-octen-2-ol, 1,2-diethoxy-3,7-dimethyl-2,6-octadiene, phenylacetaldehyde, rose oxide, ethyl 2-methylpentanoate, 1-(2,6,6-trimethyl-1,3-cyclohexadien-1-yl)-2-buten-1-one, ethyl vanillin, 2,6-dimethyl-2-octenol, 3,7-dimethyl-2-octenol, tert-butylcyclohexyl acetate, anisyl acetate, allyl cyclohexyloxyacetate, ethyllinalool, eugenol, coumarin, ethyl acetoacetate, 4-phenyl-2,4,6-trimethyl-1,3-dioxane, 4-methylene-3,5,6,6-tetramethyl-2-heptanone, ethyl tetrahydrosafranate, geranyl nitrile, cis-3-hexen-1-ol, cis-3-hexenyl acetate, cis-3-hexenyl methyl carbonate, 2,6-dimethyl-5-hepten-1-al, 4-(tricyclo[5.2.1.0]decylidene)-8-butanal, 5-(2,2,3-trimethyl-3-cyclopentenyl)-3-methylpentan-2-ol, p-tert-butyl-alpha-methylhydrocinnam-aldehyde, ethyl[5.2.1.0]tricyclodecanecarboxylate, geraniol, citronellol, citral, linalool, linalylacetate, ionone, phenylethanol and mixtures thereof.

For the purposes of the present invention, a volatile odorous substance preferably has a boiling point or boiling range below 300° C. The odorous substance is more preferably a readily volatile compound or mixture. The odorous substance particularly preferably has a boiling point or boiling range below 250° C., more preferably below 230° C., particularly preferably below 200° C.

Preference is likewise given to odorous substances which have a high volatility. The vapor pressure can be employed as a measure of the volatility. For the purposes of the present invention, a volatile odorous substance preferably has a vapor pressure of more than 0.001 kPa (20° C.). The odorous substance is more preferably a readily volatile compound or mixture. The odorous substance particularly preferably has a vapor pressure of more than 0.01 kPa (20° C.), more preferably a vapor pressure of more than 0.05 kPa (20° C.). Particular preference is given to the odorous substances having a vapor pressure of more than 0.1 kPa (20° C.).

EXAMPLES

Example 1

Atmospheric-Pressure Preparation of an Al-BDC MOF in DMF 5.8 g of terephthalic acid (BDC) and 26 g of $Al(NO_3)_3 \cdot 9H_2O$ are suspended in 100 ml of DMF and the mixture is stirred under reflux at 133° C. for 16 hours. The solid is subsequently filtered off, washed with 20 ml of methanol and dried at 200° C. in a vacuum drying oven for 16 hours. The powder is finally after-treated at 330° C. in a muffle furnace (100 l/h of air) for 3 days (heating at about 75° C./h).

7.7 g of a light-brown powder having a surface area of 1267 m²/g (determined by the Langmuir method) are obtained. The diffraction pattern (XRD) is shown in FIG. 1. For all diffraction patterns, the sample is prepared unground under an $N_2$ bell jar and coated with a Styroflex film to make it airtight. The diffraction pattern of the sample is recorded on a D5000 instrument from Siemens using a Cu anode at a step width of 0.02° and a step rate of 3.6 s.

Example 2

Atmospheric-Pressure Preparation of an Al-BDC MOF in DMF 19.9 g of terephthalic acid (BDC) and 23.3 g of $Al_2(SO_4)_3 \cdot 18H_2O$ are suspended in 100 ml of DMF and the mixture is stirred at 130° C. under reflux for 16 hours (350 rpm). The solid is subsequently filtered off, washed with 3×20 ml of DMF and 20 ml of methanol and dried at 200° C. in a vacuum drying oven for 16 hours. The powder is finally after-treated at 330° C. in a muffle furnace (100 l/h of air) for 3 days (heating at about 75° C./h).

15.7 g of product having a surface area of 1398 m²/g (determined by the Langmuir method) are obtained.

Example 3

Atmospheric-Pressure Preparation of an Al-BDC MOF in DEF 19.9 g of terephthalic acid (BDC) and 23.3 g of $Al_2(SO_4)_3 \cdot 18H_2O$ are suspended in 100 ml of DEF and the mixture is stirred at an external temperature of the oil bath of 130° C. for 16 hours (290 rpm). The mixture is then left to stand for about 60 hours at room temperature. The solid is subsequently filtered off, washed with 7×20 ml of DMF and 2×20 ml of methanol and dried at 200° C. in a vacuum drying oven for 16 hours. The powder is finally after-treated at 330° C. in a muffle furnace (100 l/h of air) for 3 days (heating at about 75° C./h).

Figure 3:
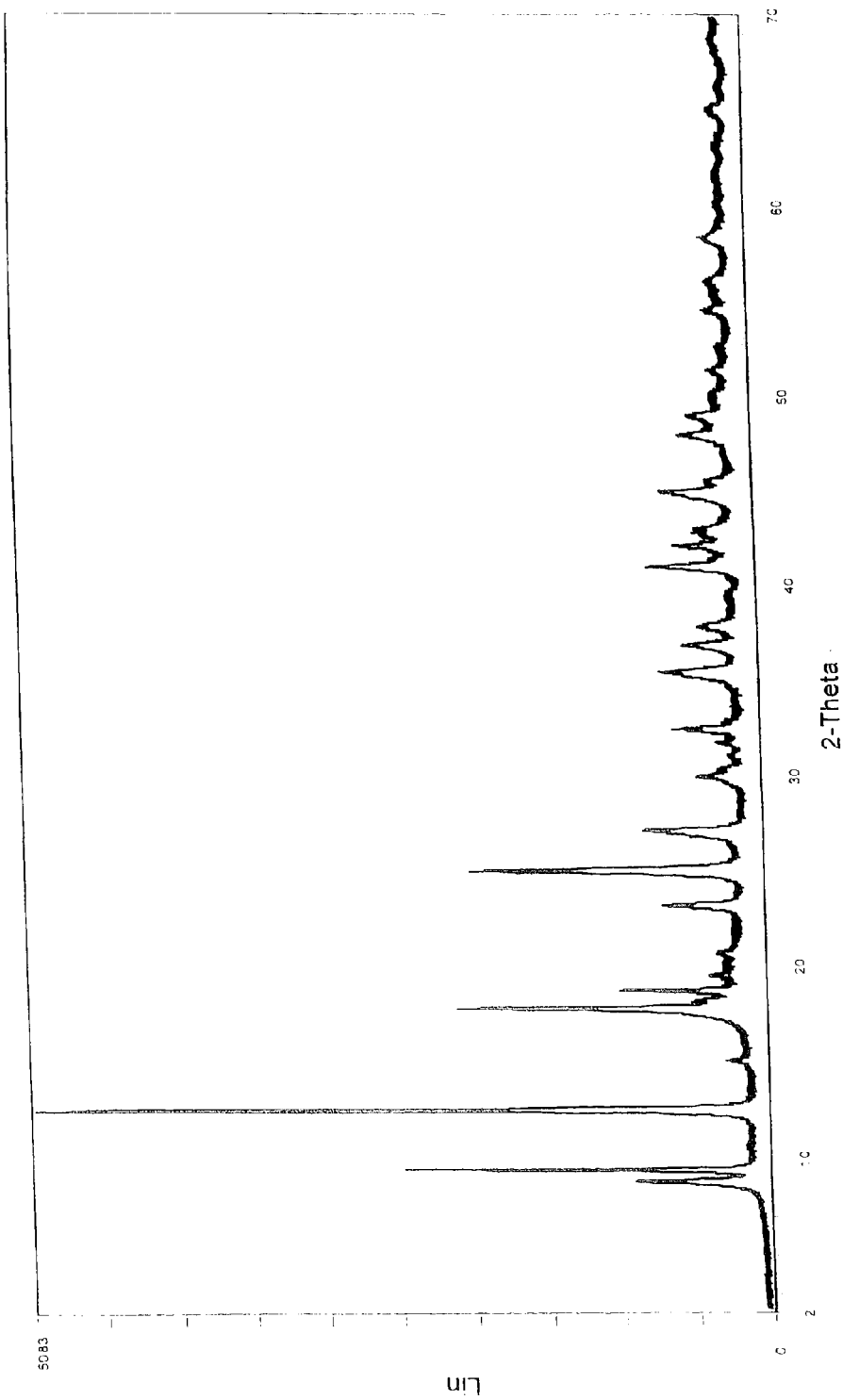
FIG. 3 The diffraction pattern (XRD) of Example 3.

16 g of product having a surface area of 1425 m²/g (determined by the Langmuir method) are obtained. The diffraction pattern (XRD) is shown in FIG. 3.

Comparative Example 4

Atmospheric-Pressure Preparation of an Al-BDC MOF in Water 5.8 g of terephthalic acid (BDC) and 23.3 g of $Al_2(SO_4)_3 \cdot 18H_2O$ are suspended in 100 ml of water and the mixture is stirred at 100° C. under reflux for 3 days (500 rpm). The mixture is then allowed to stand for about 60 hours at room temperature. The solid is subsequently filtered off, washed with 3×20 ml of water and 3×20 ml of methanol and dried at 200° C. in a vacuum drying oven for 16 hours. The powder is finally after-treated at 330° C. in a muffle furnace (100 l/h of air) for 3 days (heating at about 75° C./h).

Only 1.5 g of product having a surface area of 1416 m²/g (determined by the Langmuir method) are obtained.

Comparative Example 5

Preparation of an Al-BDC MOF in Water Under Superatmospheric Pressure and Without After-Treatment 5.76 g of terephthalic acid (BDC) and 26 g of j $Al(NO_3)_3 \cdot 9H_2O$ are suspended in 100 ml of water and the mixture is stirred for 30 minutes under ambient conditions. The mixture is subsequently maintained at 220° C. in a Berghoff autoclave (Teflon liner) for 3 days. After filtration, the solid is washed with 5×20 ml of water and dried at 330° C. in a muffle furnace (100 l/h of air) for 3 days.

Figure 2:
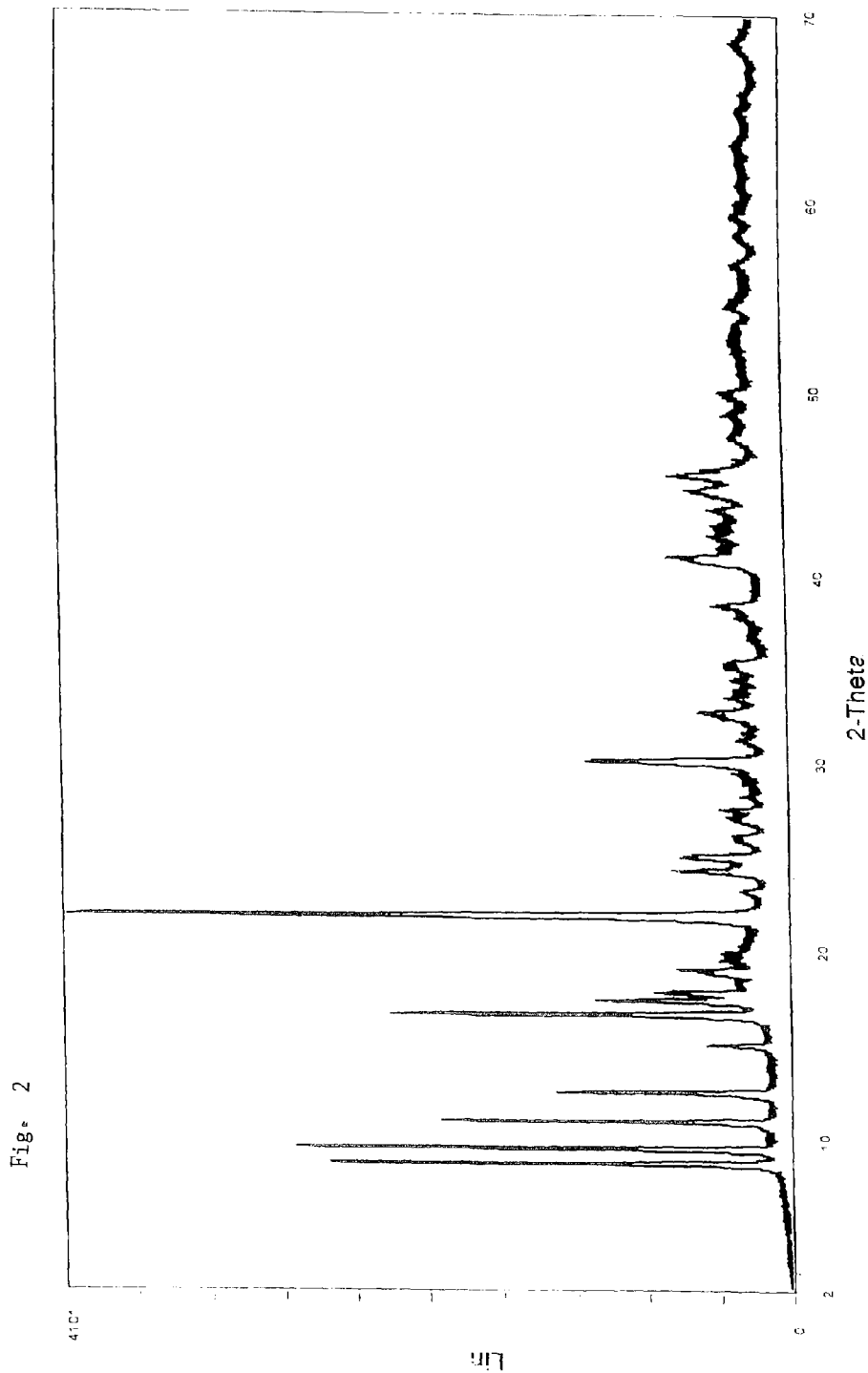
FIG. 2 The diffraction pattern (XRD) of Comparative Example 5.

Only 4.6 g of product having a surface area of 319 m²/g (determined by the Langmuir method) are obtained. The diffraction pattern (XRD) is shown in FIG. 2.

Comparative Example 6

Preparation of an Al-BDC MOF in DMF Under Superatmospheric Pressure 5.8 g of terephthalic acid (BDC) and 26 g of $Al(NO_3)_3 \cdot 9H_2O$ are suspended in 100 ml of DMF and the mixture is stirred for 10 minutes under ambient conditions. The mixture is subsequently maintained at 170° C. in a Berghoff autoclave (Teflon liner) for 1 day. After filtration, the solid is washed a number of times with DMF and subsequently a number of times with acetone. The product was firstly predried at 130° C. in a vacuum drying oven for 20 hours and dried at 330° C. in a muffle furnace (100 l/h of air) for 3 days.

7.8 g of product having a surface area of 1196 m²/g (determined by the Langmuir method) are obtained. A scale-up could not be carried out.

Example 7

Atmospheric-Pressure Preparation of an Al-BDC MOF in DMF (Scale-Up)

292.9 g of terephthalic acid (BDC) and 250.1 g of $Al_2(SO_4)_3 \cdot 18H_2O$ are suspended in 1257 g of DMF and heated at 130° C. for 24 hours while stirring. The suspension is subsequently filtered and the filter cake is washed a number of times with DMF. The filter cake is firstly predried in air for two days and subsequently dried at 320° C. in an air atmosphere in a muffle furnace for 72 hours.

192 g of product having a surface area of 1483 m²/g (determined by the Langmuir method) are obtained.

Example 8

Atmospheric-Pressure Preparation of an Al-BDC MOF 19.9 g of terephthalic acid (BDC) and 23.3 g of $Al_2(SO_4)_3 \cdot 18H_2O$ are suspended in 100 g of NMP and heated at 130° C. for 24 hours while stirring. The suspension is subsequently filtered and the filter cake is washed a number of times with NMP. The filter cake is firstly predried in air for two days and subsequently dried at 320° C. under an air atmosphere in a muffle furnace for 72 hours.

15.1 g of product having a surface area of 1134 m$^2$/g (determined by the Langmuir method) are obtained.

Example 9

Isobutene Polymerization with the Aid of the Framework from Example 3

5 g of framework are placed in a 300 ml steel autoclave and admixed with 100 g of toluene. 82 ml of liquid isobutene are injected into the closed autoclave. The autoclave was maintained at 170° C. for 3 hours. After cooling, the liquid phase is analyzed by GC (GC-% by area): inter alia, 68% of $C_4$, 26% of $C_8$ are comprised. In addition, higher olefins, for example 2.3% of $C_{16}$ and 1.7% of $C_{20}$, are also found.

Example 10

Storage of $H_2$ by the Framework from Example 7

The Al-MOF from Example 7 is evacuated at a pressure of less than 1 mbar at 80° C. for 5 hours before the measurement. 161.96 g of the dried product are transferred to an empty vessel. This is subsequently cooled to 77 K and evacuated. Hydrogen is introduced a little at a time via a gas metering device and the amount taken up is in each case determined gravimetrically. At 50.3 bar, the Al-MOF achieves a hydrogen uptake of about 3% by weight.

Example 11

Storage of Methane by the Framework from Example 7

The Al-MOF from Example 7 is evacuated at a pressure of less than 1 mbar at 80° C. for 5 hours before the measurement. 161.96 g of the dried product are transferred to an empty vessel. The temperature of this is subsequently brought to 25° C. and the vessel is evacuated. Methane was introduced a little at a time via a gas metering device and the amount taken up was in each case determined gravimetrically. At 50.4 bar, 40.3 g/l, and at 99.7 bar even 79.8 g/l, of methane could be stored in this way in the MOF-filled bottle.

Example 12

Atmospheric-Pressure Preparation of an Al-BDC MOF in DMF (Scale-Up)

398.7 g of terephthalic acid (BDC) and 466.5 g of $Al_2(SO_4)_3*18H_2O$ are suspended in 2000 ml of DMF and heated at 115° C. for 24 hours while stirring. The suspension is subsequently filtered and the filter cake is washed a number of times with 3×400 ml of DMF and 400 ml of methanol. The filter cake is then blown dry with $N_2$ for 96 hours. 375 g of product were obtained.

15 g of the dried product are extracted with methanol in a Soxhlet extractor for 48 hours and filtered off. The filter cake was washed with 3×25 ml of methanol and dried at 110° C. in a vacuum drying oven for 24 hours.

The surface area of the extracted material was 1522 m$^2$/g (determined by the Langmuir method).

Example 13

Atmospheric-Pressure Preparation of an Al-BTC MOF in DMF 7.8 g of benzenetricarboxylic acid (BTC) and 22.9 g of $Al(NO_3)_3*9H_2O$ are suspended in 520.5 g of DMF and heated at 130° C. for 4 days while stirring. The suspension is subsequently filtered and the filter cake is washed with 2×100 ml of DMF and 4×100 ml of methanol. The filter cake is then dried at 200° C. in a vacuum drying oven for 16 hours. The powder is finally after-treated at 330° C. in a muffle furnace (100 l/h of air) for 3 days (heating at about 75° C./h).

8.4 g of product having a surface area of 1791 m$^2$/g (determined by the Langmuir method) are obtained.

Example 14

Atmospheric-Pressure Preparation of an Al-BDC MOF in DMF 7.8 g of benzenetricarboxylic acid (BTC) and 14.7 g of $AlCl_3*6H_2O$ are suspended in 520.5 g of DMF and heated at 130° C. for 4 days while stirring. The suspension is subsequently filtered and the filter cake is washed with 2×100 ml of DMF and 4×100 ml of methanol. The filter cake is then dried at 200° C. in a vacuum drying oven for 16 hours. The powder is finally after-treated at 330° C. in a muffle furnace (100 l/h of air) for 3 days (heating at about 75° C./h).

10.9 g of product having a surface area of 1451 m$^2$/g (determined by the Langmuir method) are obtained.

Comparative Example 15

Atmospheric-Pressure Preparation of an Al-BTC MOF in Water 7.8 g of benzenetricarboxylic acid (BTC) and 22.9 g of $Al(NO_3)_3*9H_2O$ are suspended in 130.8 g of water and heated at 100° C. for 4 days while stirring. The suspension is subsequently filtered and the filter cake is washed with water. The filter cake is dried at 150° C. in a vacuum drying oven for 2 days.

Only 0.6 g of product is obtained.

Comparative Example 16

Hydrothermal Preparation of an Al-BTC MOF in $H_2O$ 7.8 g of benzenetricarboxylic acid (BTC) and 22.9 g of $Al(NO_3)_3*9H_2O$ are suspended in 130.8 g of water and heated at 130° C. in a Berghoff autoclave (Teflon liner) for 4 days. The suspension is subsequently filtered and the filter cake is washed with water. The filter cake is dried at 150° C. in a vacuum drying oven for 2 days.

Only 0.4 g of product is obtained.

Example 17

Example 18

Preparation of an Al-BDC MOF in DMF 250.1 g of terephthalic acid (BDC) and 292.9 g of $Al_2(SO_4)_3*18H_2O$ are suspended in 1257 g of DMF and heated at 130° C. for 24 hours while stirring. The suspension is subsequently filtered and the filter cake is washed with DMF. The filter cake is dried at 120° C. in a vacuum drying oven for 2 hours.

One half of the dried filter cake is subsequently calcined at 250° C. in a drying oven for 24 hours. The weight loss is 38.6%. A product having a surface area of 634 $m^2/g$ is formed.

The other half is calcined at 320° C. in a muffle furnace for 3 hours. The weight loss is 59.8%. A product having a surface area of 1368 $m^2/g$ is formed.

Example 19

Figure 4:
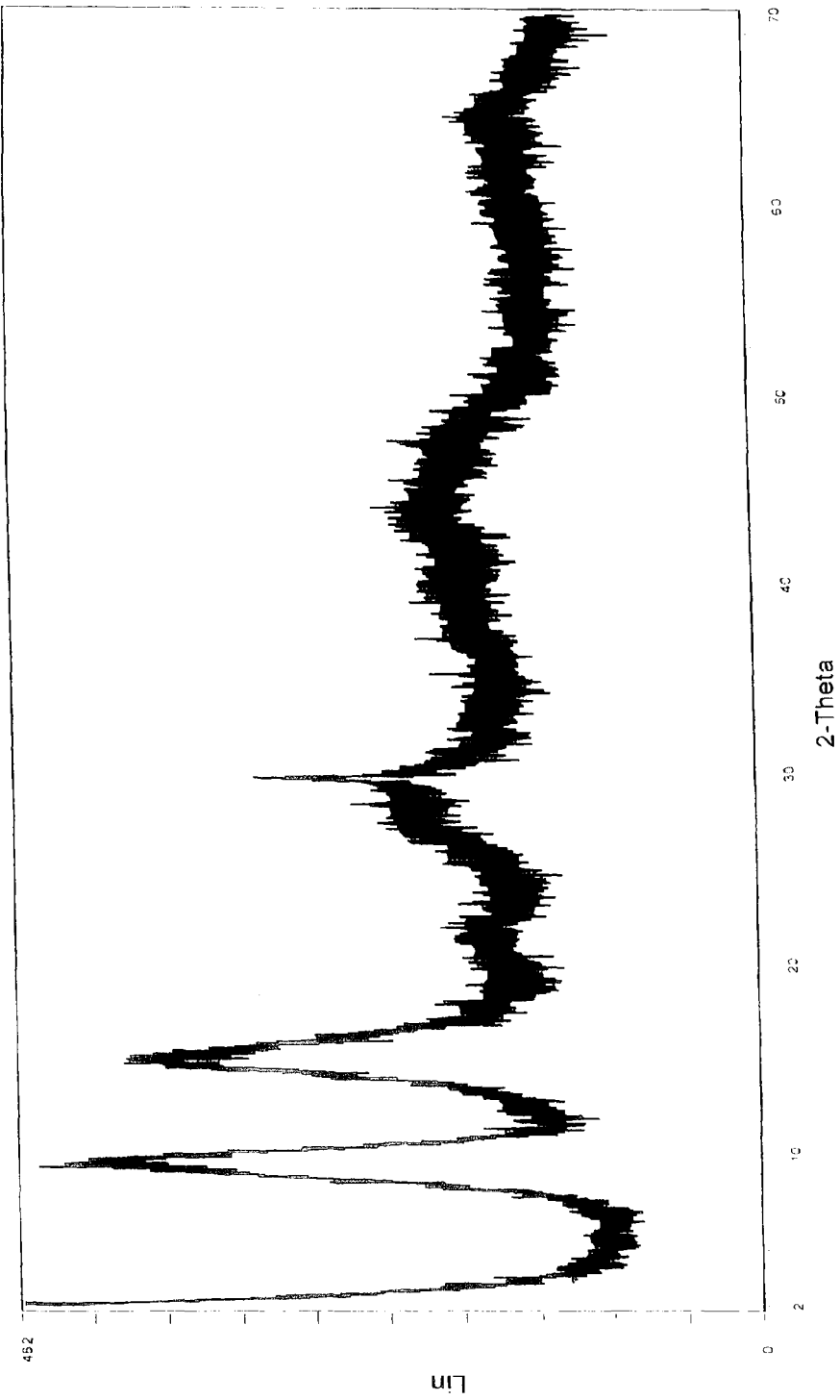
FIG. 4 The diffraction pattern (XRD) of Example 19.

Atmospheric-Pressure Preparation of an Al-camphordioic acid MOF in DEF 7.4 g of (+)-camphordioic acid and 24 g of $Al(SO_4)_3*18H_2O$ are suspended in 520.5 g of DEF and heated at 130° C. for 4 days while stirring. The suspension is subsequently filtered and the filter cake is washed with 2×100 ml of DEF and 4×100 ml of methanol. The filter cake is dried at 200° C. in a vacuum drying oven for 16 hours. 11.8 g of a product having a surface area of 429 $m^2/g$ (determined by the Langmuir method) are obtained. The diffraction pattern (XRD) is shown in FIG. 4. 1.5 g of the product are extracted in boiling methanol in a Soxhlet apparatus for 16 hours and subsequently dried at room temperature under reduced pressure. The surface area is improved to 555 $m^2/g$.

Example 20

Atmospheric-Pressure Preparation of an Al-butanetetracarboxylic acid MOF in DEF 8.7 g of 1,2,3,4-butanetetracarboxylic acid and 48 g of $Al(SO_4)_3*18H_2O$ are suspended in 520.5 g of DEF and heated at 130° C. for 4 days while stirring. The suspension is subsequently filtered and the filter cake is washed with 2×100 ml of DEF and 4×100 ml of methanol. The filter cake is dried at 200° C. in a vacuum drying oven for 16 hours. 14.9 g of a product having a surface area of 518 $m^2/g$ (determined by the Langmuir method) are obtained.

Example 21

Figure 5:
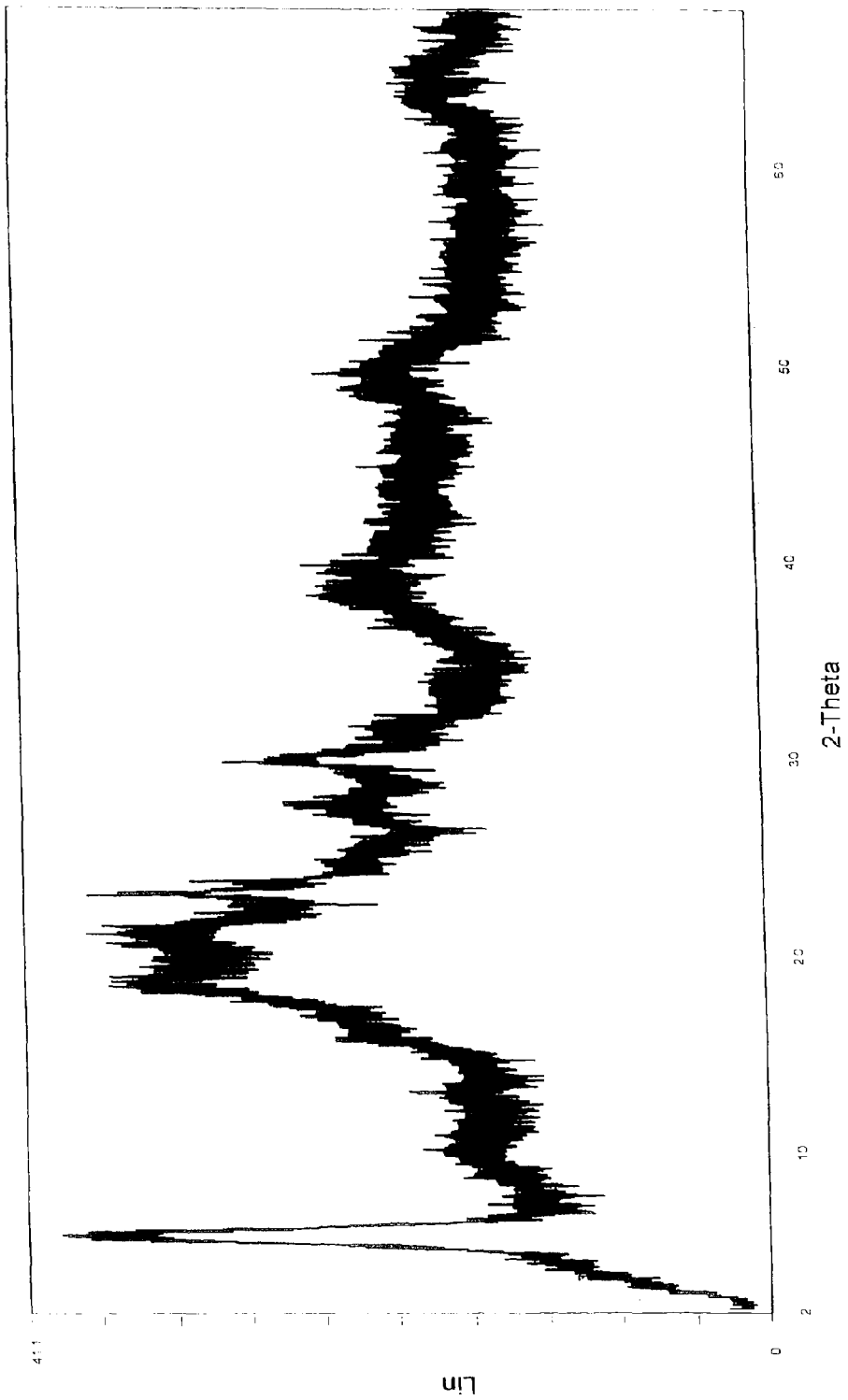
FIG. 5 The diffraction pattern (XRD) of Example 21.

Atmospheric-Pressure Preparation of an Al-mercaptosuccinic acid MOF in DEF 5.6 g of mercaptosuccinic acid and 27.8 g of $Al(NO_3)_3*9H_2O$ are suspended in 520.5 g of DEF and heated at 130° C. for 3 days while stirring. The suspension is subsequently filtered and the filter cake is washed with 2×100 ml of DEF and 4×100 ml of methanol. The filter cake is dried at 200° C. in a vacuum drying oven for 16 hours. 7.8 g of a product having a surface area of 488 $m^2/g$ (determined by the Langmuir method) are obtained. The diffraction pattern (XRD) is shown in FIG. 5.

Example 22

Atmospheric-Pressure Preparation of an Al-1,4-naphthalenedicarboxylic acid MOF in DMF 8 g of 1,4-naphthalenedicarboxylic acid and 27.8 g of $Al(NO_3)_3*9H_2O$ are suspended in 520.5 g of DMF and heated at 130° C. for 3 days while stirring. The suspension is subsequently filtered and the filter cake is washed with 3×100 ml of methanol. The filter cake is dried at 200° C. in a vacuum drying oven for 16 hours. 8.7 g of a product are obtained. 1.5 g are subsequently extracted with methanol in a Soxhlet extractor for 16 hours and dried at room temperature under reduced pressure for 16 hours.

A specific surface area of 752 $m^2/g$ is obtained.

Example 23

Atmospheric-Pressure Preparation of a Mg-2,6-naphthalenedicarboxylic acid MOF in DEF 4.9 g of 2,6-naphthalenedicarboxylic acid and 8.16 g of $Mg(NO_3)_2*6H_2O$ are suspended in 1686 g of DEF and heated at 105° C. for 24 hours while stirring. The suspension is subsequently filtered and the filter cake is washed firstly with DMF and subsequently with chloroform. The filter cake is dried in air. 4.8 g of product are obtained. The dried product is calcined at 330° C. in a muffle furnace for 2 days.

Figure 6:
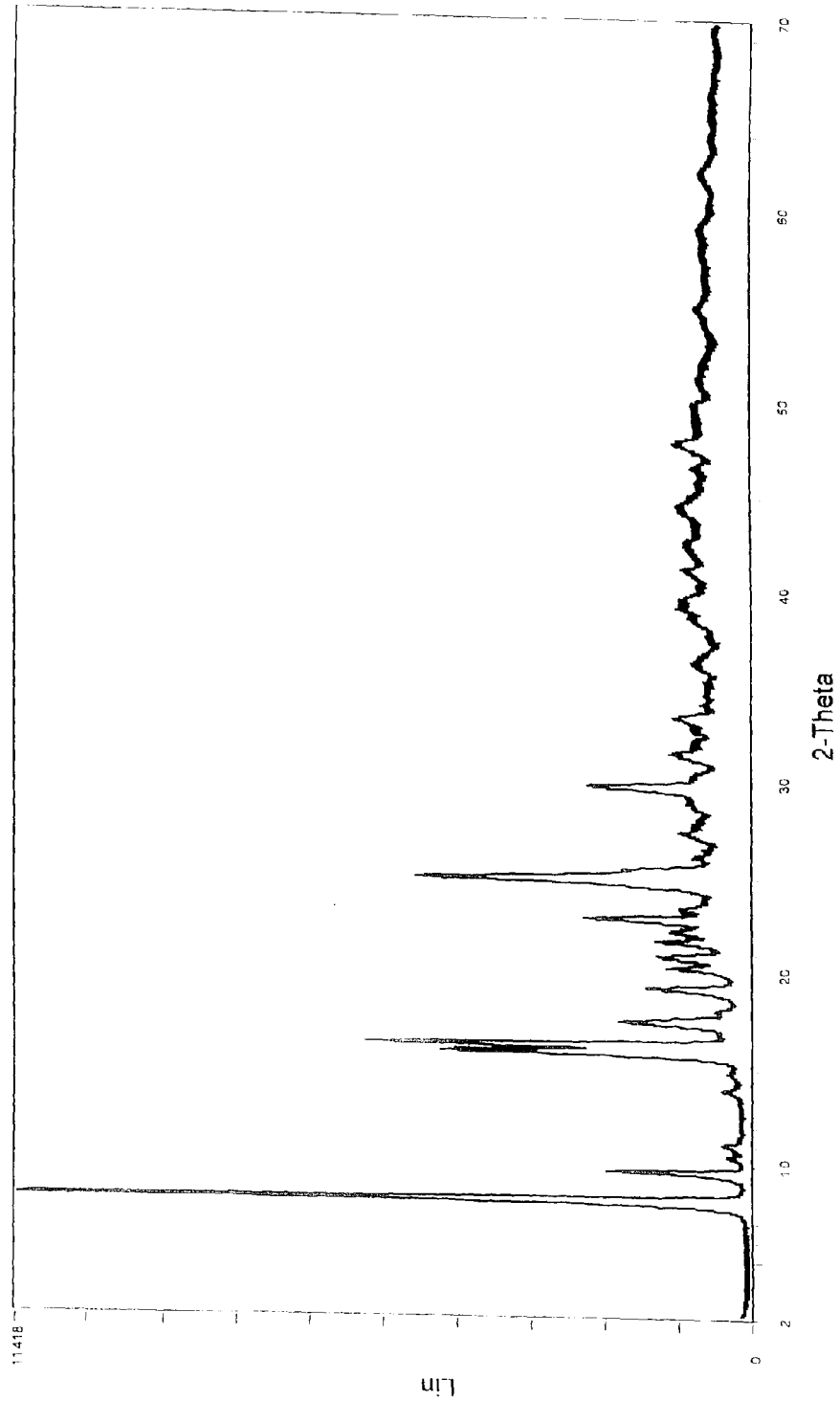
FIG. 6 The diffraction pattern (XRD) of Example 23.

3.6 g of product are obtained. The diffraction pattern (XRD) is shown in FIG. 6. The product is a crystalline substance having a diffraction pattern typical of MOFs.

Example 24

Preparation of an Al-1,2,4,5-benzenetetracarboxylic acid MOF 9.4 g of 1,2,4,5-benzenetetracarboxylic acid and 30.5 g of $Al(NO_3)_3*9H_2O$ are suspended in 520.5 g of DMF in a 1 stirred flask, heated to 130° C. and maintained under these conditions for 72 hours while stirring. The precipitated product is filtered off, washed with 2×100 ml of DMF and 4×100 ml of methanol and dried at 200° C. in a vacuum drying oven for 16 hours. The product is finally calcined at 330° C. under air atmosphere in a muffle furnace for 72 hours.

12.8 g of product having an $N_2$ surface area of 930 $m^2/g$ (determined by the Langmuir method) are obtained.

Example 25

Preparation of an Al-mercaptosuccinic acid MOF 13.6 g of mercaptosuccinic acid and 67.6 g of $Al(NO_3)_3*9H_2O$ are suspended in 1246 g of DMF in a 2 stirred flask, heated to 130° C. and maintained under these conditions for 72 hours while stirring. The precipitated product is filtered off, washed with 1×200 ml of DMF and 3×200 ml of methanol and dried at 200° C. in a vacuum drying oven for 16 hours.

17.7 g of a yellowish product having an $N_2$ surface area of 551 $m^2/g$ (determined by the Langmuir method) are obtained.

Example 26

Preparation of an Al-terephthalic acid MOF 239 kg of terephthalic acid and 279 kg of $Al_2(SO_4)_3*18H_2O$ are suspended in 1500 kg of DMF, heated to 130° C. and maintained under these conditions for 18 hours while stirring. The precipitated product is filtered off, washed with 3×500 of acetone. The filter cake is subsequently resuspended twice in 500 of methanol at 60° C. for 3 hours and the methanol is subsequently filtered off again. The filter cake is subsequently dried under reduced pressure, initially at 50° C. and later at 100° C.

Figure 7:
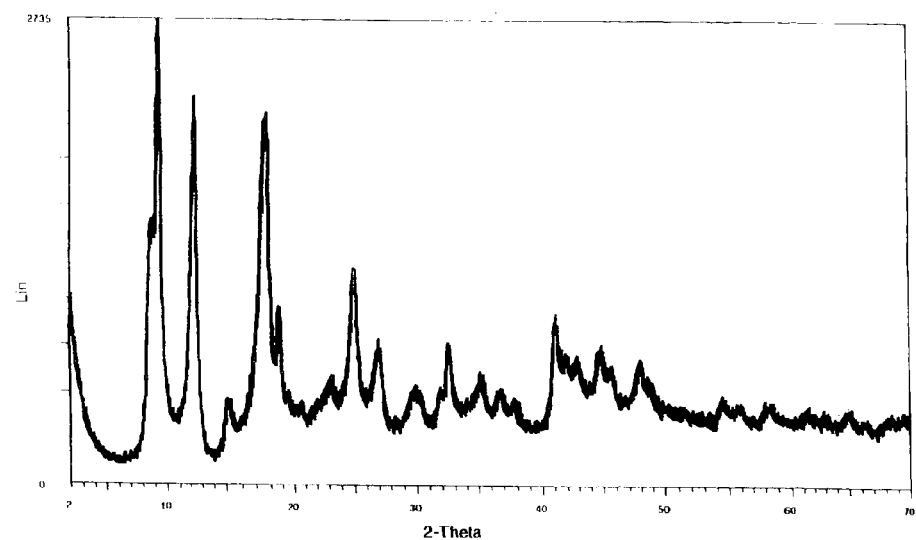
FIG. 7 The diffraction pattern (XRD) of Example 26.

249 kg of a white material are obtained. After a subsequent treatment at 360° C. under an air atmosphere in a muffle furnace for 48 hours, the material has an $N_2$ surface area of 1400 $m^2/g$. The XRD is shown in FIG. 7.

Example 27

Preparation of an Al-isophthalic acid MOF 7.23 g of isophthalic acid and 7.0 g of $AlCl_3*6H_2O$ are suspended in 300 ml of DMF in a stirred flask, heated to 130° C. and maintained under these conditions for 20.5 hours while stirring. The precipitated product is filtered off, washed with 3×50 ml of DMF and 4×50 ml of methanol and dried at 110° C. in a vacuum drying oven for 16 hours.

Figure 8:
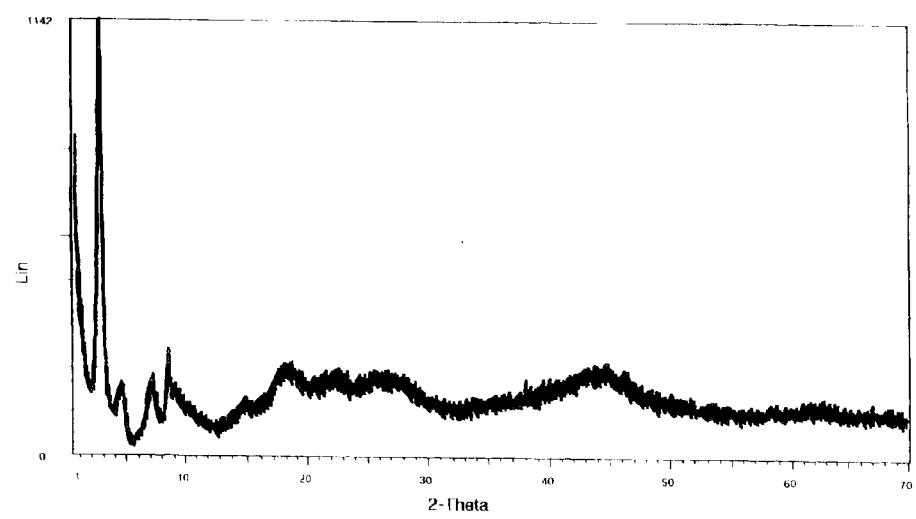
FIG. 8 The diffraction pattern (XRD) of Example 27.

3.94 g of a yellow product having an $N_2$ surface area of 1242 $m^2/g$ (determined by the Langmuir method; activation temperature: 150° C.) are obtained. According to elemental analysis, the material comprises 42.8% of C, 8.8% of Al and 4.5% of H. The XRD is shown in FIG. 8.

Example 28

Preparation of an Al-4,5-imidazoledicarboxylic acid MOF 5.17 g of 4,5-imidazoledicarboxylic acid and 5.33 g of $AlCl_3*6H_2O$ are suspended in 300 ml of DMF in a stirred flask, heated to 130° C. and maintained under these conditions for 20.5 hours while stirring. The precipitated product is filtered off, washed with 3×50 ml of DMF and 4×50 ml of methanol and dried at 110° C. in a vacuum drying oven for 72 hours.

3.94 g of a pale orange product having an $N_2$ surface area of 703 $m^2/g$ (determined by the Langmuir method; activation temperature: 150° C.) are obtained. According to elemental analysis, the material comprises 35.3% of C, 8.5% of Al and 3.7% of H.

Example 29

Preparation of an Al-cyclohexane-dicarboxylic acid MOF 1.33 g of cyclohexanedicarboxylic acid (cis/trans mixture) and 5.95 g of $Al(NO_3)_3*9H_2O$ are suspended in 111 g of DMF in a stirred flask, heated to 130° C. and maintained under these conditions for 17 hours while stirring. The precipitated product is filtered off, washed with 2×50 ml of DMF and 4×50 ml of methanol and dried at 130° C. in a vacuum drying oven for 16 hours.

Figure 9:
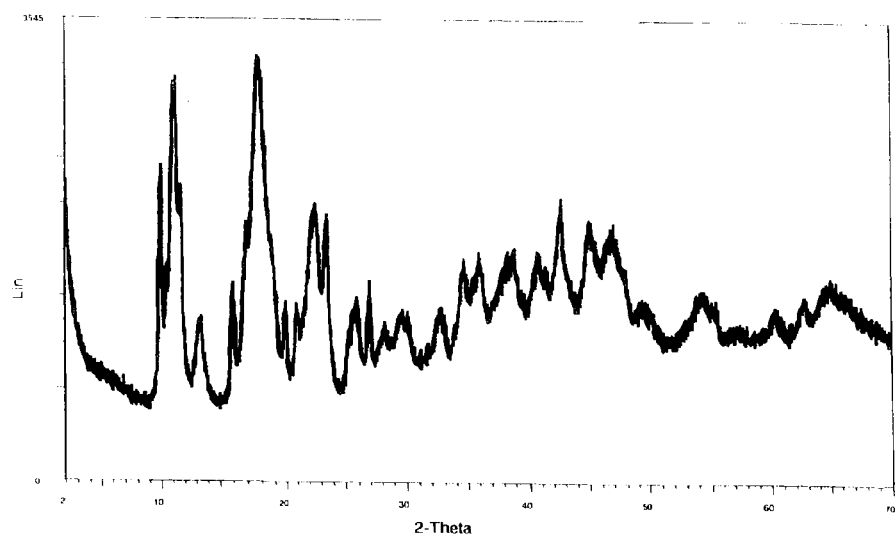
FIG. 9 The diffraction pattern (XRD) of Example 29.

3.94 g of a white product having an $N_2$ surface area of 410 $m^2/g$ (determined by the Langmuir method) are obtained. The XRD is shown in FIG. 9.

Example 30

Preparation of an Mg-naphthalenedicarboxylic acid MOF 6.66 g of 2,6-naphthalenedicarboxylic acid and 10.98 g of $Mg(NO_3)_2*6H_2O$ are suspended in 137 g of DMF in a stirred flask, heated to 130° C. and maintained under these conditions for 48 hours while stirring. The water formed in the reaction is driven off via a distillation attachment by means of a stream of $N_2$. The precipitated product is filtered off, washed twice with DMF and twice with chloroform. The filter cake is firstly dried at room temperature and finally calcined at 250° C. for 48 hours.

Figure 10:
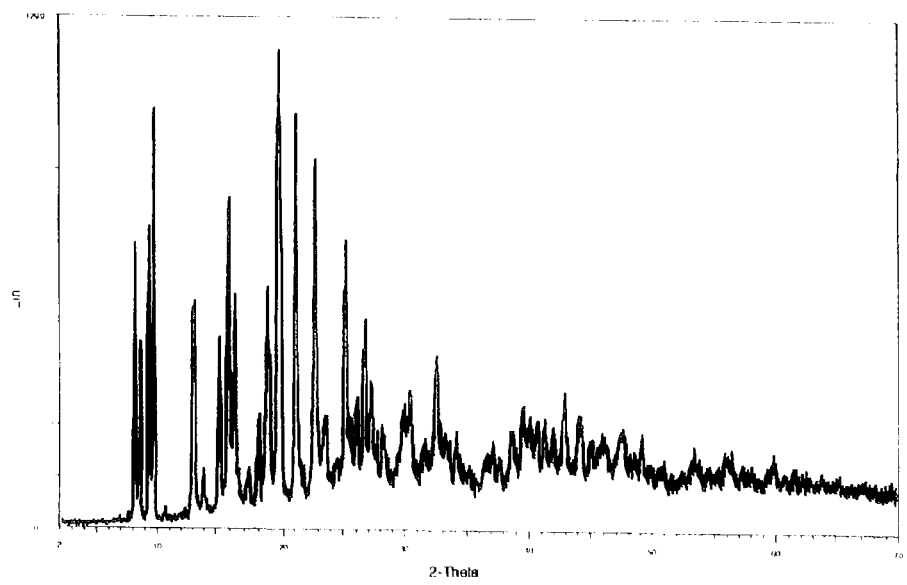
FIG. 10 The diffraction pattern (XRD) of Example 30 in dried form.
Figure 11:
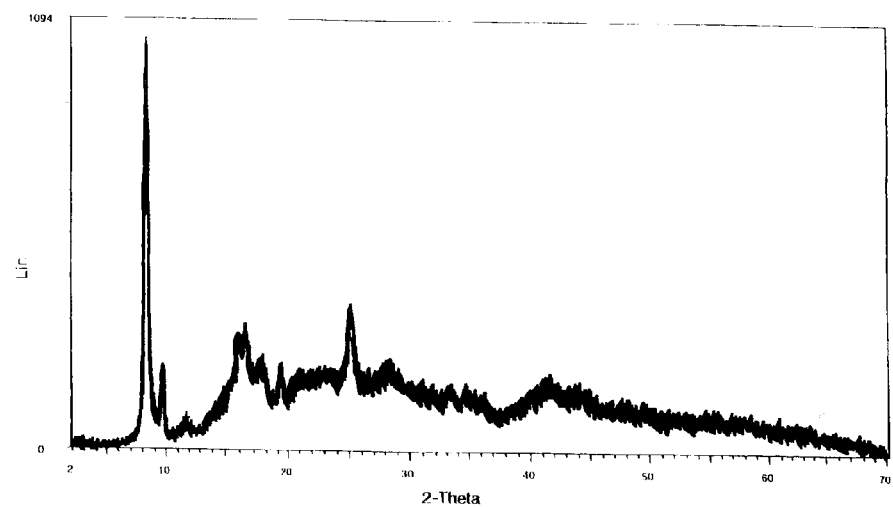
FIG. 11 The diffraction pattern (XRD) of Example 30 in calcined form.

7.8 g of product are obtained after drying and 5.4 g of product are obtained after calcination. The calcined form has an $N_2$ surface area (determined by the Langmuir method) of 294 $m^2/g$. FIG. 10 shows the XRD of the dried form, and FIG. 11 shows that of the calcined form.

Example 31

Preparation of a Ca-5-tert-butylisophthalic acid MOF 4.95 g of 5-tert-butylisophthalic acid and 9.75 g of $CaCl_2*6H_2O$ are suspended in 312.3 g of DMF in a stirred flask, heated to 130° C. and maintained under these conditions for 20 hours while stirring. The precipitated product is filtered off, washed with 1×50 ml of DMF and 3×50 ml of methanol and dried at 200° C. in a vacuum drying oven for 10 hours.

Figure 12:
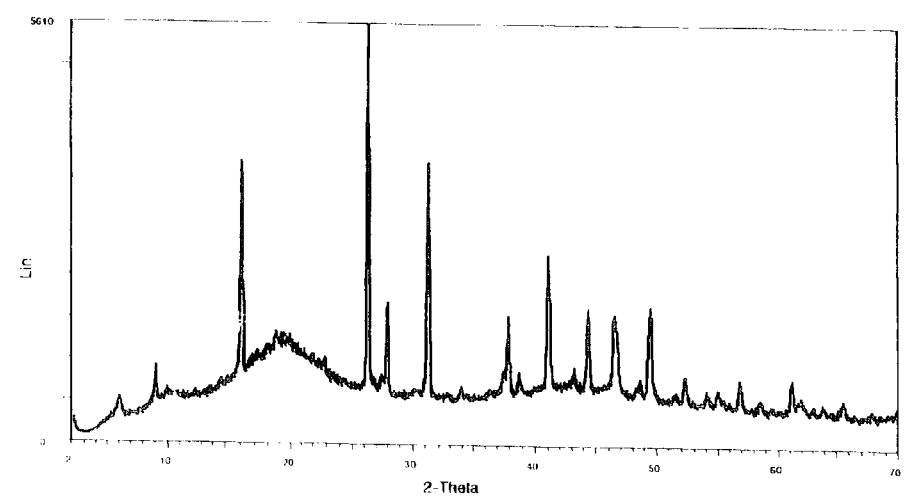
FIG. 12 The diffraction pattern (XRD) of Example 31.

4.9 g of a product are obtained. The $N_2$ surface area is 5 $m^2/g$ (determined by the Langmuir method)—the product here is obviously an MOF having only a low porosity or very narrow pores. The XRD is shown in FIG. 12.

The invention claimed is:

1. A process for preparing a porous metal-organic framework, which comprises:
   reacting, with stirring and at a pressure of not more than 2 bar (absolute), at least one metal compound with at least one at least bidentate organic compound which can coordinate to the metal, in the presence of a nonaqueous organic solvent selected from the group consisting of DMF, DEF, and NMP, to form a porous metal-organic framework,
   where the metal is $Mg^{II}$, or $Al^{III}$ and the organic compound has at least two atoms which are selected independently from the group consisting of oxygen, sulfur and nitrogen and via which the organic compound can coordinate to the metal,
   wherein the at least bidentate organic compound is a dicarboxylic, or tricarboxylic acid, and
   wherein the reaction is carried out without additional base.

2. The process according to claim 1, wherein the reaction is carried out at not more than 1230 mbar (absolute).

3. The process according to claim 1, wherein the metal is $Al^{III}$.

4. The process according to claim 1, wherein the metal compound is nonionic and/or the counterion to the metal cation is derived from a protic solvent.

5. A porous metal-organic framework obtained by a process according to claim 1.

6. The framework according to claim 5 which has a specific surface area of more than 10 $m^2/g$ determined by the Langmuir method.

7. A method comprising uptaking at least one substance by contacting said substance with a porous metal-organic framework according to claim 5.

8. The method according to claim 7, wherein the metal is $Al^{III}$ or $Mg^{II}$ and the substance is hydrogen.

9. The process according to claim 1, wherein the reaction is carried out at atmospheric pressure.

10. The process according to claim 1, wherein the metal-organic framework comprises no boron or phosphorus atoms.

11. The process according to claim 1, wherein said porous metal-organic framework is in the form of powder and has a specific surface area, calculated by the Langmuir model in accordance with DIN 66135, of greater than 500 $m^2/g$.

12. The process according to claim 1, wherein said porous metal-organic framework is in the form of powder and has a specific surface area, calculated by the Langmuir model in accordance with DIN 66135, of greater than 1000 $m^2/g$.

13. The process according to claim 1, wherein said porous metal-organic framework is in the form of powder and has a specific surface area, calculated by the Langmuir model in accordance with DIN 66135, of greater than 1250 $m^2/g$.

14. The process according to claim 1, further comprising after the reaction the framework formed is calcined at a temperature above 250° C.

15. The process according to claim 14, wherein the framework formed is calcined at 300-400° C.

16. The process according to claim 1, wherein the metal is $Mg^{II}$.

17. The process according to claim 1, wherein the metal is $Al^{III}$.

* * * * *